United States Patent
Mathisen et al.

(10) Patent No.: US 6,896,902 B2
(45) Date of Patent: May 24, 2005

(54) EFFERVESCENT SOLID COMPOSITION OF MATTER

(75) Inventors: Torbjörn Mathisen, Älvsjö (SE); Marcus Back, Vällingby (SE); Åsa Hellman, Upplands Väsby (SE)

(73) Assignee: MEDICARB AB, Bromma (SE)

( * ) Notice: Subject to any disclaimer, the term of this patent is extended or adjusted under 35 U.S.C. 154(b) by 0 days.

(21) Appl. No.: 10/120,607

(22) Filed: Apr. 12, 2002

(65) Prior Publication Data

US 2003/0026837 A1 Feb. 6, 2003

Related U.S. Application Data

(60) Provisional application No. 60/284,922, filed on Apr. 20, 2001.

(30) Foreign Application Priority Data

Apr. 12, 2001 (SE) .............................. 0101307

(51) Int. Cl.[7] .............................. A61K 9/14; A61K 9/20; A61K 9/46; A61K 9/48
(52) U.S. Cl. ...................... 424/466; 424/451; 424/465; 424/489
(58) Field of Search ................................ 424/466, 488, 424/451, 465, 464, 489

(56) References Cited

U.S. PATENT DOCUMENTS

| | | | | |
|---|---|---|---|---|
| 4,296,209 A | * | 10/1981 | Tomic | ........................ 521/85 |
| 4,572,906 A | * | 2/1986 | Sparkes et al. | ............... 514/21 |
| 2003/0206958 A1 | * | 11/2003 | Cattaneo et al. | ............ 424/488 |

FOREIGN PATENT DOCUMENTS

| | | | |
|---|---|---|---|
| JP | 63010715 | * | 1/1998 |
| WO | WO 96/02258 | | 2/1996 |
| WO | WO 96/02260 | | 2/1996 |
| WO | WO 96/022260 | * | 2/1996 |
| WO | 98/48627 | | 11/1998 |
| WO | WO 00/24785 | * | 5/2000 |

OTHER PUBLICATIONS

Novasso Novamic™: comparison between MCCh and chitosan [online]. [Retrieved on Jul. 2002]. Retrieved from the Internet: <URL: http://www.novasso.fi/comparison.html>.

* cited by examiner

Primary Examiner—James M. Spear
(74) Attorney, Agent, or Firm—Burns, Doane, Swecker & Mathis, LLP

(57) ABSTRACT

An effervescent solid composition of matter is provided, which comprises, as an active component, a substance selected from chitosan, its derivatives and salts thereof and a second component capable of releasing $CO_2$ in an acidic environment.

Also, methods for treatment of a mammal suffering from a dermal wound, or for prophylactic or wound-healing treatment of lactating animals prone to develop or suffering from mastitis, are provided. The methods comprise the steps of:

a) admixing said effervescent solid composition of matter with an aqueous liquid to form a solution or suspension thereof;

b) contacting said animals with said solution or suspension to provide such treatment.

46 Claims, No Drawings

EFFERVESCENT SOLID COMPOSITION OF MATTER

Priority is claimed under 35 U.S.C. §119(a) for the filing of Swedish Application No. 0101307-7 on Apr. 12, 2001, and under 35 U.S.C. §119(e) for the filing of U.S. Provisional Application No. 60/284,922 on Apr. 20, 2001.

FIELD OF INVENTION

The present invention relates to solid compositions of matter comprising an anti-microbial substance based on chitosan, its derivatives or salts thereof. The invention also involves a method for prophylactic or wound-healing treatment of lactating animals.

BACKGROUND OF THE INVENTION

The main active principle in the solid composition of matter involved in the present invention is selected from chitosan, its derivatives or salts thereof. Chitosan is a well-known polysaccharide which is composed of β(1-4)-linked N-acetyl-D-glucosamine and D-glucosamine units. Chitosan is manufactured by alkaline treatment of chitin, a polymer forming the shell of inter alia insects and crustaceans. Commercially, chitosan is recovered from crab- and shrimpshells that are waste products from the fishing industry. When treating chitin with alkali, usually sodium hydroxide, N-deacetylation takes place, i e acetamido groups are converted to amino groups, as the chitin is transformed to chitosan. By controlling the alkaline treatment of chitin it is possible to manufacture chitosans with varying degrees of N-acetylation.

Physical properties of chitosan, its derivatives and salts thereof, which properties affect its utility, depend on the degree of N-acetylation, the $\overline{Mw}$, the molecular weight distribution and the distribution of N-acetyl groups. Furthermore, different acid addition salts and derivatives of chitosan exhibit different properties.

It is also known that chitosan, its derivatives and salts thereof are biologically active and inter alia show anti-microbial properties.

Chitosan and derivatives and salts thereof are used in many forms, such as in solutions for the control of microbial growth. Examples of such solutions are solutions used as teat-dipping agents to prevent onset of mastitis in lactating cattle, as in e g WO 98/48627, as well as solutions for other anti-microbial uses.

One problem encountered in the use of solutions of chitosan, or of derivatives or salts thereof, is lack of stability of such solutions, especially when stored at elevated temperatures.

The dissolution of chitosan, or of derivatives or salts thereof, or indeed of any polysaccharide, is often problematic when performed without vigorous stirring. Instead of dissolving, the polysaccharide material will form lumps with a gel-like shell efficiently prohibiting further dissolution of the material.

Furthermore, transportation of dilute solutions of chitosan, or of derivatives or salts thereof, is expensive and involves handling problems in preparation and use. Also, storage facilities for dilute solutions can be costly and therefore disadvantageous.

Another possibility to solve storage and transportation problems would be to prepare concentrated solutions. However, this is not possible since chitosan forms very viscous solutions already at a low concentration, preventing the preparation of highly concentrated solutions. Another problem with chitosan solutions, and especially concentrated solutions, is that the viscosity decreases over time, due to hydrolytic degradation.

SUMMARY OF THE INVENTION

The present invention has for a main object to provide effervescent solid compositions of matter comprising, as an active principle, a substance selected from chitosan, its derivatives and salts thereof.

Another object of the invention is to provide such a composition of matter, thereby avoiding transportation and storage of aqueous solutions or suspensions of the active principle, since such solutions or suspensions can be easily prepared by the consumer at the time of use.

Yet another object of the invention is to provide such compositions of matter, which are stable in storage for a prolonged time before use thereof.

A further object of the invention is to provide solid compositions of matter comprising a substance selected from chitosan, its derivatives and salts thereof, which substances are otherwise not readily dissolved or suspended, which compositions are readily dissolved or suspended in aqueous liquid.

Still another object of the invention is to provide effervescent solid compositions of matter comprising, in addition to a substance selected from chitosan, its derivatives and salts thereof, a substance selected from heparin, heparan sulfate, dextran sulfate and other negatively charged polysaccharides or polymers.

A further object of the invention is to provide solid compositions of matter, such that solutions or suspensions made thereof, when used as teat-dipping agents, upon drying will form films on the areas treated.

Another object of the present invention is the provision of methods for wound-healing treatment of mammals.

Still another object of the invention is to provide a method for prophylactic or wound-healing treatment of lactating animals prone to develop or suffering from mastitis, particularly cows.

For these and other objects which will be evident from the following disclosure, the present invention provides an effervescent solid composition of matter comprising as an active component a substance selected from chitosan, its derivatives and salts thereof and a second component capable of releasing $CO_2$ in an acidic environment.

The composition of matter according to the invention preferably contains less chitosan, or derivative or salt thereof, than 50% by weight of chitosan, more preferably less than 25% by weight of chitosan. In keeping with the objects of the invention, this preferred proportion of chitosan, or derivative or salt thereof, in the composition of matter is mainly dictated by the capacity for dissolution or suspension of the active ingredient by the second component and the acidic environment, when the composition is placed in an aqueous liquid. The content of chitosan, or of derivatives or salts thereof, has to be sufficiently low, compared to the content of effervescing components in the composition of matter, for dissolution to occur. The percentage referred to above is thus the percentage of chitosan in relation to effervescing components. Surprisingly, it has been found by the present inventors that the relation between the quantity of effervescence-generating components and chitosan, or derivatives or salts thereof, is critical for the dissolution of the composition in an aqueous liquid. As stated above, most chitosan qualities will not dissolve without vigorous stirring, even in large amounts of aqueous liquid and after long times. This also holds true if the proportion of chitosan is too large in relation to the quantity of effervescing components. The dissolution rate of chitosan, or derivatives or salts thereof, in the composition of matter according to the invention thus depends on efficient mixing caused by release of $CO_2$ from the effervescent components, as well as on the final pH of the solution, as described in detail below.

If chitosan derivatives or salts are used that are more easily dissolved than chitosan itself, the percentage thereof may be increased. The same is true for chitosan, or derivatives or salts thereof, of different molecular weights, low-molecular weight qualities being more easily dissolved or suspended.

The preferred quality of the chitosan, or derivative or salt thereof, used in the composition of matter according to the invention depends on the specific area of use. This in turn will influence the concentration of chitosan, or derivative or salt thereof, that is preferred.

To obtain maximum anti-microbial efficiency, in those embodiments of the invention where this is desired, it is preferred that the chitosan, or derivative or salt thereof, has a degree of deacetylation of no less than about 50%, preferably no less than about 80% and particularly no less than about 85%. However, an upper limit of the deacetylation degree of about 95% is preferred, mainly due to practical and economic aspects of the preparation of chitosan, or derivative or salt thereof. Thus, a preferred composition of matter according to the invention comprises chitosan, or derivative or salt thereof, having a deacetylation degree within the range from about 85% to about 95%, but the upper limit of 95% may be exceeded by compositions that still come within the scope of the present invention. This may occur for example if an economical process of obtaining chitosan of such high degree of deacetylation is made available. Then, chitosan having a deacetylation degree of up to 99% or more may be obtainable, and may well be used in compositions according to the present invention.

The viscosity of an aqueous solution of a certain concentration of chitosan, or derivative or salt thereof, can be modified by using qualities of chitosan, its derivatives or salts thereof with different weight average molecular weights ($\overline{Mw}$), In the present invention, chitosan, or derivative or salt thereof, with a molecular weight of between 1 kDa and 2000 kDa is preferred.

The preferred particle size of the chitosan, or derivative or salt thereof, used is less than 850 $\mu$m, more preferably less than 250 $\mu$m (60 mesh). If chitosan, or derivative or salt thereof, of another particle size is used, ox if the molecular weight of the chitosan, or derivative or salt thereof, is such that dissolution of particles is difficult, the particles may be ground to a smaller size prior to use.

In a composition of matter according to the invention, said second component is preferably a carbonate, e g selected from alkali metal carbonates, alkali metal bicarbonates, alkaline earth metal carbonates, alkaline earth metal bicarbonates, ammonium carbonate, and ammonium bicarbonate.

Said second component has the capacity to release $CO_2$ in an acidic environment. This acidic environment may be provided as an aqueous solution with a low pH, e g an acetic acid solution, in which the composition of matter is placed, In preferred embodiments, however, release of $CO_2$ is obtained through the use of a third component of the solid composition, which is selected from solid acids and mixtures thereof.

In such embodiments, said second and third component of the composition of matter according to the invention can be regarded as an "effervescent couple". The effervescent couple thus comprises at least one component capable of releasing $CO_2$ in an acidic environment (the second component of the composition of matter) and at least one solid acid (the third component), preferably a solid organic acid. The couple renders effervescence upon mixing with an aqueous solution, as the components of the couple combine to produce carbon dioxide. The effervescing action also aids in mixing the other ingredients of the composition to achieve even dispersion and solubilisation throughout the solution.

In those embodiments of the invention that employ a solid acid, or mixture of solid acids, as a third component, it is preferred to use a solid organic acid, or mixtures of solid acids comprising at least one solid organic acid. Preferably, this is a weak organic acid that provides a certain buffering effect resulting in a less varying pH in a solution or suspension prepared by dissolution or suspension of the solid composition according to the invention. For the purposes of preparing a solution or suspension for use on the teats of lactating animals, a non-toxic, mono-carboxylic acid, e g a non-toxic $\alpha$-hydroxy acid, is preferred, glycolic acid being the most preferred for this application, In other applications, the preferred solid organic acid may be an $\alpha$-hydroxy acid or an acid other than $\alpha$-hydroxy acids, including ascorbic acid. In most biological applications, the solid acid will need to exhibit properties such as non-toxicity and pharmaceutical acceptability. The $pK_a$ of the solid acid is preferably below 7, a $pK_a$ below 5 being even more preferred.

A particularly preferred composition of matter according to the invention is constituted by the active component being selected from chitosan, its derivatives and salts thereof, the second component being an alkali metal bicarbonate, and the composition further comprising a third component which is glycolic acid.

In the composition of matter according to the invention, the contents of acid thereof is preferably in stoichiometric excess over the contents of said second component.

Where the active component is an acid addition salt of chitosan and the composition contains a solid acid, or mixture of solid acids, as third component, said stoichiometric excess is based on said third component together with the acid of addition.

Where the composition of matter according to the invention contains chitosan as such as active principle and a solid acid, or mixture of solid acids, as third component, said stoichiometric excess refers to the contents of the third component over the second component.

The composition of matter, according to those embodiments of the invention that contain a solid acid, or mixture of solid acids, as third component, preferably has an acid content such that, when the composition is dissolved or suspended in the appropriate amount of aqueous liquid, the pH of the solution or suspension is below about 7, so that the chitosan of the composition is readily dissolved. More preferably, the pH value is in the range of from about 2 to about 6.8, the lower limit being dictated mainly by the desired properties of the solution or suspension. For applications wherein the solution or suspension is to be applied to the skin of an animal or human subject, the pH range is even more preferably from about 4 to about 6.8, the lower limit here being dictated by the sensitivity of the area to which the solution or suspension is to be applied.

When the composition is dissolved or suspended in the appropriate amount of liquid, the pH of the solution or suspension can optionally be further stabilised by use of a pH buffering system, which in certain applications of the present invention will need to be non-toxic and pharmaceutically acceptable. Examples of preferred buffering systems include the acetic acid system and buffer systems of other monovalent acids, e g lactic acid.

The acidic pH of the liquid provides a suitable environment for dissolution or suspension of chitosan, or of a derivative or salt thereof, as well as a suitable environment for $CO_2$ release from the second component. Inventively, these two effects operate in a synergistic manner to facilitate the dissolution or suspension of chitosan, or derivative or salt thereof, in the liquid.

The composition of matter according to the invention may additionally contain heparin, heparan sulfate, dextran sulfate or another negatively charged polysaccharide or polymer. It may also be preferred to include neutral polymers, e g cellulose, in the composition of matter according to the invention, since such polymers may confer desired properties to a solution or suspension made from the composition, in terms of e g improved clarity or viscosity.

The composition of matter according to the present invention can be presented in different forms, e g powder, granules, pellets, capsules or tablets of suitable size, prepared by standard methods well known to the skilled person. An additional component of the composition, e g any of the negatively charged polysaccharides mentioned in the previous paragraph, may be added as a separated coating around a core consisting of the main components of the composition of matter, forming a dragée, or as a part of a tablet containing more than one compartment.

The composition of matter according to the present invention may optionally further comprise pharmaceutically acceptable excipients known to the skilled person, e g binders, diluents, surfactants, lubricants, disintegrants, antimicrobial agents, detergents and colouring agents.

The composition of matter according to the present invention is preferably kept in moisture-proof or airtight packages or containers, e g welded aluminum containers, etc. Transportation of products in a dry form and in moisture-proof packets makes it more difficult to contaminate the product. Further, such compositions are much less expensive to transport than compositions in liquid form. In many cases, the effectiveness of active ingredients is prolonged in a dry, rather than liquid, state due to increased stability of the ingredients in the dry state.

The composition of matter according to the invention is thus especially practical when it is used for the preparation of solutions or suspensions, which retain their activity for only a short time after preparation thereof, since said solutions or suspensions may be prepared shortly or even immediately before use, According to one preferred embodiment, the composition of matter according to the present invention is kept in one separate, moisture-proof container, while an effervescent composition of matter comprising heparin, heparan sulfate, dextran sulfate or another negatively charged polysaccharide or polymer is kept in another separate container. Thus, the contents of the two containers may be used simultaneously or at separate instants. Another possibility is the provision, in such a second, separate container, of a liquid, e g glycerol, that confers desired properties, e g a skin conditioning effect, to the resulting solution or suspension.

The composition of matter according to the present invention can be used as a medicament. In particular, the composition of matter according to the present invention can be used for the manufacture of an aqueous solution or suspension for treatment of dermal wounds in mammals including man. Furthermore, the composition of matter according to the present invention can advantageously be used for the manufacture of an aqueous solution or suspension for prophylactic or wound-healing treatment of mastitis in lactating animals.

The present invention also relates to a method for treatment of a mammal suffering from a dermal wound, which method comprises the steps of:
  a) admixing an effervescent solid composition of matter according to the present invention with an aqueous liquid to form a solution or suspension thereof;
  b) contacting the dermal wound of said mammal with said solution or suspension to provide such treatment.

The present invention also relates to a method for prophylactic or wound-healing treatment, or both, of a lactating animal prone to develop or suffering from mastitis. The method comprises the steps of:
  a) admixing an effervescent solid composition of matter according to the present invention with an aqueous liquid to form a solution or suspension thereof;
  b) contacting teats of said animal with said solution or suspension to provide such treatment.

The methods according to the invention, described immediately above and having regard to mastitis, suitably take place in connection with milking operations. Considering the daily milking, the application is suitably performed twice or thrice a day after milking. In certain cases it may be preferable to apply the solution before milking, considering the risk of transferring microorganisms during the milking process. The method of the invention is very well suited for such a pre-milking treatment, as the risk of transferring non-desirable components into the milk is minimized through the use of a chitosan-containing solution or suspension. Chitosan, or derivative or salt thereof, is preferably present in the solution or suspension in an anti-microbial active concentration.

Preferably, in the methods of the invention, an effervescent composition of matter is used which comprises components that provide a skin conditioning effect on skin. Such components may be glycolic acid as the third component, or glycerol as an additive, but other skin conditioning components are possible.

In such methods it is preferred that said composition of matter is used in an amount resulting in a solution or suspension having a concentration of chitosan of up to and including about 2% (weight/volume), the upper limit being mainly dictated by economic and practical considerations, The most preferable concentration of chitosan in said solution or suspension is about 1% (w/v).

A particularly preferred composition of matter for use in the methods for prophylactic or wound-healing treatment according to the invention comprises a combination of chitosan, or derivative or salt thereof, and one or more of the additional substances heparin, heparan sulfate and dextran sulfate, whereby solutions or suspensions made thereof when used as teat-dipping agents upon drying will form particularly water-resistant films on the areas treated.

Other applications of use for the composition of matter according to the invention than that of the methods described above are possible. In such applications, solutions or suspensions having even lower concentrations, e g down to about 0.1% (w/v) of chitosan, may prove active and effective. In such cases, lower concentrations naturally offer advantages in terms of economy.

EXAMPLES OF PREFERRED EMBODIMENTS

The present invention will in the following be illustrated in connection with non-limiting examples. In said examples parts and percentages refer to weight if not otherwise stated.

Compositions with other dissolution times than those reported can easily be prepared by changing the ratio between chitosan, or derivative or salt thereof, and effervescent couple. The form of the composition of matter, e g powder, granules, pellets, capsules or tablets, will also affect the dissolution time. Also, the pressure applied when preparing tablets affects the dissolution time of a resulting tablet.

Materials

The chitosan used in the following examples was of commercial grade, having a deacetylation degree of 84–99%. Likewise, the heparin used was of commercial grade.

Tablet Experiment

Examples 1–5

Preparation of Tablets

The tablets of the examples below were prepared in laboratory scale by mixing and grinding of the included chemicals into fine particles. For compression of standard size tablets, a standard FTIR press was used. Larger tablets were compressed in a specially adapted press made from a plastic tube with a lid and bottom. Materials were transferred into the tube and the lid fitted. The device was then placed in a press designed for production of FTIR tablets, whereupon the materials were compressed at approximately 3 tons for 30–60 seconds.

The tablets of the examples below had diameters in the range from about 13 to about 40 mm, with thicknesses of about 2, 3 or 7 mm, depending on the amount of material present in the tablet.

Dissolution times refer to solutions that are not stirred during dissolution of tablets.

Example 1

The compositions of Table 1 were prepared by mixing chitosan or an acid addition salt thereof with a solid acid and sodium bicarbonate. solid preparations of powder or tablets were formed as described above,

TABLE 1

| Composition | Chitosan (g) | Chitosan · HCl (g) | Acid | Sodium bicarbonate (g) |
|---|---|---|---|---|
| A | | 1.0 | 2.0 g glycolic acid | 2.0 |
| B | 1.0 | | 2.2 g glycolic acid | 2.0 |
| C | | 1.0 | 1.6 g benzoic acid | 1.0 |
| D | | 1.0 | 1.8 g salicylic acid | 1.0 |
| E | | 1.0 | 5.6 g ascorbic acid | 2.4 |
| F | 1.0 | | 20 g citric acid | 1.8 |
| G | | 3.0 | 3.0 g glycolic acid | 3.0 |
| H | 1.0 | | 2.0 g glycolic acid | 1.8 |
| J | 0.5 | | 1.0 g glycolic acid | 0.9 |
| K | 2.0 | | 4.0 g glycolic acid | 3.5 |
| L | 1.0 | | 2.3 g glycolic acid | 2.0 |

Example 2

The solid compositions A–F of Table 1 were admixed with 100 ml tap water at ambient temperature. The solid composition G of Table 1 was admixed with 300 ml tap water at ambient temperature. Thus, chitosan or its acid addition salt was added in an amount corresponding to 1.0% (weight/volume) of the total volume. The time from addition of the composition until it was fully dissolved was recorded and is shown Table 2, as is the pH value of each resultant solution.

TABLE 2

| Composition | pH | Dissolution time (h) |
|---|---|---|
| A | 4.7 | 1 |
| B | 5.5 | 0.8 |
| C | 5.2 | over night[a] |
| D | 4.9 | over night[a] |
| E | 5.1 | 5[b] |
| F | 2.3 | 0.03 |
| G | 4.7 | 5.5 |

[a]Not completely dissolved after 2 h, completely dissolved after 16 h
[b]Most of the material is dissolved after 10 minutes, completely dissolved after 5 h

Example 3

The solid compositions H–K of Table 1 were admixed with 100 ml tap water at ambient temperature. Thus, chitosan was added in an amount corresponding to from 0.5% to 2.0% (w/v) of the total volume. The time from addition of the composition until it was fully dissolved was recorded and is shown in Table 3, as is the pH value of each resultant solution.

TABLE 3

| Composition | % Chitosan | pH | Dissolution time (h) |
|---|---|---|---|
| H | 1.0 | 5.3–5.5 | 0.8 |
| J | 0.5 | 5.5–5.8 | 0.2 |
| K | 2.0 | 5.3–5.4 | 1.5 |

Example 4

A tablet was prepared containing 0.02 g heparin, 0.1 g glycolic acid, and 0.1 g sodium bicarbonate. The tablet was dissolved in 100 ml tap water at ambient temperature. The solid composition L of Table 1 was admixed with the solution.

Thus, chitosan was added in an amount corresponding to 1.0% (w/v) of the total volume. The time from addition of the composition until it was fully dissolved was approximately 45 minutes. The resulting solution contained 1.0% (w/v) chitosan and 0.02% (w/v) heparin, pH 5.0.

Example 5

A tablet was prepared containing 1.0 g chitosan and 1.75 g sodium bicarbonate. The tablet was dissolved in 100 ml of a solution of 6% acetic acid at ambient temperature.

The tablet was completely dissolved in approximately 10 minutes.

Granulation Experiment

Examples 6–17

In all of the examples below, chitosan granulate is added to water in an amount yielding solutions of 1% by weight of chitosan. In those cases (examples 12–17) where heparin is added to water, the amount thereof corresponds to 0.02% by weight in the final solutions.

Example 6

100.3 g chitosan, 198.0 g glycolic acid and 175.3 g $NaHCO_3$ were mixed for one minute in a Kenwood mixer, and granulated with 21.5 g of an aqueous solution of ethanol (70%). The granulate was dried in a heating cabinet for 4 h at 50° C., and then sieved through a 1.3 mm hand sieve. Finally, the granulate was mixed for 40 minutes in a Turbula mixer.

When 4.7 g of the granulate was dissolved in 100 ml of water, a yellow solution was obtained. With stirring, the granulate was dissolved within 30 seconds. Some foaming occurred.

Example 7

49.9 g chitosan and 99.3 g glycolic acid were mixed for one minute in a Kenwood mixer, and granulated with about 9 g of an aqueous solution of ethanol (70%). The granulate was dried in a heating cabinet for 3 h at 50° C., and then sieved through a 1.3 mm hand sieve. 87.8 g $NaHCO_3$ was added, and the final granulate was mixed for 20 minutes in a Turbula mixer.

The granulate exhibited a strong effervescent reaction when mixed with water, dissolving in a clear, slightly yellow solution.

Example 8

50.0 g chitosan and 88 g $NaHCO_3$ were mixed in a Turbula mixer for 10 minutes. 99.3 g glycolic acid were added, and the mixing was continued for another 10 minutes. Subsequently, the mixture was sieved through a 1.3 mm sieve.

The granulate was relatively easily dissolved in water, and a slightly yellow and not completely clear solution was obtained.

Example 9

49.6 g chitosan, 50.1 g lactose, 99.7 g glycolic acid and 87.8 g $NaHCO_3$ were granulated with 17 g of an aqueous solution of ethanol (70%) in a Kenwood mixer. The resulting granulate was dried for 4 h at 50° C. in a drying cabinet. Finally, the granulate was sieved through a 1.3 mm sieve.

When enough granulate was added to water to form a 1% chitosan solution, part of the granulate floated on the surface of the water, and it was necessary to aid dissolution by stirring.

Example 10

100 g chitosan and 150 g lactose were granulated with 100 g of an aqueous povidone solution (10%) in a Kenwood mixer. The granulate was dried for 2.5 h at 50° C. in a drying cabinet, before being sieved through a 1.5 mm sieve.

50 g of the resulting granulate, 45 g glycolic acid and 35 g $NaHCO_3$ were then mixed in a Turbula mixer for 10 minutes. 6.5 g of the mixture was added to 100 ml of water, giving a solution of 1% by weight chitosan. The granulate dissolved fast during intensive foaming when stirred, giving an almost clear solution with a pH of 3.7.

Example 11

50 g chitosan, 100 g lactose and 120 g glycolic acid were granulated with 72 g of an aqueous solution of ethanol (70%) in a Kenwood mixer. The granulate was dried for 4 h at 50° C. in a driving cabinet, before being sieved through a coarse sieve.

5.4 g of the resulting granulate was mixed with 1.7 g $NaHCO_3$. When placed in water, this mixture was relatively easily dissolved. Some of the material sunk to the bottom of the vessel, and a calm effervescent reaction started. All of the material was dissolved after one hour, yielding a solution with a pH of 4.4. After 24 h the solution was totally clear and the pH value 4.24.

Examples 12–17

Preparation of Heparin Granules:

2.00 g heparin and 10.0 g lactose were mixed with a spoon. 2 g of an aqueous povidone solution (20%) was added as granulation liquid during stirring using a nozzle. The resulting granulate was dried for 2 h at 60° C. in a drying cabinet and then sieved through a 1.5 mm sieve, yielding a fine white-grey powder.

Preparation of Chitosan Granules:

50 g chitosan, 100 g lactose and 120 g glycolic acid were granulated with 72 g of an aqueous solution of ethanol (70%) in a Kenwood mixer. The granulate was dried for 4 h at 50° C. in a drying cabinet, before being sieved through a coarse sieve.

Preparation of Chitosan-Heparin Solutions:

In examples 12–17, 0.12 g of the heparin granulate obtained above was placed in 100 ml of distilled water at a temperature of 22° C. pH measurements were used to monitor the dissolution process. Next, the chitosan granulate obtained above was added. In examples 12, 14 and 16, the chitosan granulate was mixed with $NaHCO_3$ prior to addition of the powder to the heparin solution. In examples 13, 15 and 17, the $NaCHO_3$ was added separately a few seconds after the addition of chitosan to the heparin solution.

The results are shown in Table 4 below. In all examples, the material was totally dissolved, yielding solutions of 0.02% by weight of heparin and 1% by weight of chitosan.

TABLE 4

| Example | Heparin granulate (g) | pH of heparin solution | Chitosan granulate (g) | $NaHCO_3$ (g) | $NaHCO_3$ Addition | pH (minutes after addition) |
|---|---|---|---|---|---|---|
| 12 | 0.12 | 6.8 | 5.4 | 1.7 | Mixed dry with the chitosan granulate | 5.4 (30) |
| 13 | 0.12 | 7.7 | 5.4 | 1.7 | Separately | 4.3 (45) |
| 14 | 0.12 | — | 5.4 | 1.5 | Mixed dry with the chitosan granulate | 4.7 (—) |
| 15 | 0.12 | 6.7 | 5.4 | 1.7 | Separately | 4.1 (90) |
| 16 | 0.12 | 6.9 | 5.4 | 2.1 | Mixed dry with the chitosan granulate | 5.2 (90) |
| 17 | 0.12 | 7.2 | 5.4 | 2.1 | Separately | 5.5 (90) |

What is claimed is:

1. An effervescent solid composition comprising:
   (i) a first component which is an active agent selected from the group consisting of chitosan, chitosan derivatives, and salts thereof;
   (ii) a second component capable of releasing $CO_2$ in an acidic environment; and
   (iii) a third component selected from solid acids or mixtures thereof;
   wherein the effervescent solid composition has a pH from about 2 to about 6.8 when dissolved in an aqueous solution.

2. The composition of claim 1, wherein said active component is a salt of chitosan.

3. The composition of claim 1, wherein said active component is chitosan.

4. An effervescent solid composition comprising:
   (i) a first component which is an active agent selected from the group consisting of chitosan, chitosan derivatives, and salts thereof;

(ii) a second component capable of releasing $CO_2$ in an acidic environment;

(iii) a third component selected from solid acids or mixtures thereof; and (iv) heparin, heparan sulfate, dextran sulfate, another negatively charged polysaccharide, or a negatively charged polymer;

wherein the effervescent solid composition has a pH from about 2 to less than 7 when dissolved in an aqueous solution.

5. The composition of claim 1, wherein said second component is a carbonate.

6. The composition of claim 5, wherein said carbonate is selected from the group consisting of alkali metal carbonates, alkali metal bicarbonates, alkaline earth metal carbonates, alkaline earth metal bicarbonates, ammonium carbonate, and ammonium bicarbonate.

7. The composition of claim 4, wherein the pH is in the range from about 2 to about 6.8.

8. The composition of claim 1, wherein the pH is in the range from about 4 to about 6.8.

9. An effervescent solid composition comprising:

(i) a first component which is an active agent selected from the group consisting of chitosan, chitosan derivatives, and salts thereof;

(ii) a second component capable of releasing $CO_2$ in an acidic environment; and (iii) a third component selected from solid acids or mixtures thereof;

wherein the effervescent solid composition has a pH from about 2 to less than 7 when dissolved in an aqueous solution, and wherein the acid content, originating from said third component plus any acid addition salt of chitosan, is in stoichiometric excess over said second component.

10. The composition of claim 1, wherein said third component is selected from the group consisting of organic solid acids and mixtures thereof.

11. The composition of said claim 10, wherein said third component is a α-hydroxy acid.

12. The composition of claim 11, wherein said third component is glycolic acid.

13. An effervescent solid composition comprising:

(i) a first component which is a chitosan;

(ii) a second component which is an alkali metal bicarbonate; and (iii) a third component which is glycolic acid;

wherein the effervescent solid composition has a pH from about 2 to less than 7 when dissolved in an aqueous solution.

14. The composition of claim 1 in the form of powder, granules, pellets, capsules, or tablets.

15. The composition of claim 1 further comprising a pharmaceutically acceptable excipient.

16. The composition of claim 4, wherein said active component is a salt of chitosan.

17. The composition of claim 9, wherein said active component is a salt of chitosan.

18. The composition of claim 4, said active component is chitosan.

19. The composition of claim 9, wherein said active component is chitosan.

20. The composition of claim 4, said second component is a carbonate.

21. The composition of claim 20, wherein said carbonate is selected from the group consisting of alkali metal carbonates, alkali metal bicarbonates, alkaline earth metal carbonates, alkaline earth metal bicarbonates, ammonium carbonate, and ammonium bicarbonate.

22. The composition of claim 9, wherein said second component is a carbonate.

23. The composition of claim 22, wherein said carbonate is selected from the group consisting of alkali metal carbonates, alkali metal bicarbonates, alkaline earth metal carbonates, alkaline earth metal bicarbonates, ammonium carbonate, and ammonium bicarbonate.

24. The composition of claim 9, wherein the pH is from about 2 to about 6.8.

25. The composition of claim 13, wherein the pH is from about 2 to about 6.8.

26. The composition of claim 7, wherein the pH is from about 4 to about 6.8.

27. The composition of claim 24, wherein the pH is from about 4 to about 6.8.

28. The composition of claim 25, wherein the pH is from about 4 to about 6.8.

29. The composition of claim 1, wherein the acid content, originating from said third component and an acid addition salt of chitosan, is in stoichiometric excess over said second component.

30. The composition of claim 4, wherein the acid content, originating from said third component and an acid addition salt of chitosan, is in stoichiometric excess over said second component.

31. The composition of claim 13, wherein the acid content, originating from said third component, is in stoichiometric excess over said second component.

32. The composition of claim 4, wherein said third component is selected from the group consisting of organic solid acids and mixtures thereof.

33. The composition of claim 32, wherein said third component is a α-hydroxy acid.

34. The composition of claim 33, wherein said third component is glycolic acid.

35. The composition of claim 9, wherein said third component is selected from the group consisting of organic solid acids and mixtures thereof.

36. The composition of claim 35, wherein said third component is a α-hydroxy acid.

37. The composition of claim 36, wherein said third component is glycolic acid.

38. The composition of claim 4, wherein said composition is in the form of powder, granules, pellets, capsules, or tablets.

39. The composition of claim 9, wherein said composition is in the form of powder, granules, pellets, capsules, or tablets.

40. The composition of claim 13, wherein said composition is in the form of powder, granules, pellets, capsules, or tablets.

41. The composition of claim 4, further comprising a pharmaceutically acceptable excipient.

42. The composition of claim 9, further comprising a pharmaceutically acceptable excipient.

43. The composition of claim 13, further comprising pharmaceutically acceptable excipient.

44. The composition of claim 1, additionally containing heparin, heparan sulfate, dextran sulfate, another negatively charged polysaccharide, or a negatively charged polymer.

45. The composition of claim 9, additionally containing heparin, heparan sulfate, dextran sulfate, another negatively charged polysaccharide, or a negatively charged polymer.

46. The composition of claim 13, additionally containing heparin, heparan sulfate, dextran sulfate, another negatively charged polysaccharide, or a negatively charged polymer.

* * * * *